United States Patent [19]

Ehrhardt et al.

[11] Patent Number: 4,829,075

[45] Date of Patent: May 9, 1989

[54] ANTIMYCOTIC 1,1-DISUBSTITUTED CYCLOPROPANE DERIVATIVES

[75] Inventors: Heinz Ehrhardt, Rehling; Ernst Blume, Kriftel; Wolfgang Raether, Dreieich; Walter Dittmar, Hofheim am Taunus, all of Fed. Rep. of Germany

[73] Assignee: Hoechst Aktiengesellschaft, Frankfurt am Main, Fed. Rep. of Germany

[21] Appl. No.: 25,581

[22] Filed: Mar. 13, 1987

[30] Foreign Application Priority Data

Mar. 15, 1986 [DE] Fed. Rep. of Germany ....... 3608727

[51] Int. Cl.$^4$ .................. A01N 43/50; A01N 43/653; A01N 43/80

[52] U.S. Cl. ................................ 514/340; 514/341; 514/378; 514/383; 514/396; 514/397; 514/399; 546/276; 546/278; 548/247; 548/248; 548/262; 548/336; 548/342; 548/346

[58] Field of Search ............... 548/262, 341, 247, 248, 548/336, 342, 346; 546/276, 278; 514/340, 341, 378, 383, 397, 399, 396

[56] References Cited

FOREIGN PATENT DOCUMENTS 0088050 9/1983 European Pat. Off. .

OTHER PUBLICATIONS

*Chemical Abstracts* 134289f, vol. 87, 1977 [Jonczyk, A., et al., *Rocz. Chem.* 1977, 51(1), 175–179].

*Primary Examiner*—Richard A. Schwartz
*Attorney, Agent, or Firm*—Finnegan, Henderson, Farabow, Garrett, & Dunner

[57] ABSTRACT

Compounds I

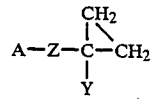

where

A equals t-butyl, phenyl, biphenylyl, phenoxyphenyl, benzylphenyl, benzyloxyphenyl, phenylthiophenyl, phenylsulfinylphenyl, phenylsulfonylphenyl, naphthyl, 1,2,3,4-tetrahydronaphthyl, indanyl, fluorenyl, thienyl, furyl, pyridyl, isoxazolyl, pyrazolyl, benzofuryl or benzothienyl, Z equals CO, $CH_2$ or radicals of ketone derivatives;

Y equals azole or equals —X—$R^8$ ($R^8$=(cyclo)alkyl or an aromatic) or equals a number of amine derivatives or equal acyl, are antimycotics. The preparation and use as medicaments are described.

6 Claims, No Drawings

ANTIMYCOTIC 1,1-DISUBSTITUTED CYCLOPROPANE DERIVATIVES

The invention relates to 1,1-disubstituted cyclopropane derivatives having antimycotic properties, and also to processes for the preparation thereof. The compounds are likewise valuable intermediates for the preparation of other biologically active substances.

1-Methyl- and 1-phenylthio-1-benzoylcyclopropane are known from CA 87, 134 289 f, without mention of the use or biological action.

EP-A No. 088,050 discloses photocurable dyed materials comprising (a) an olefinically unsaturated, photopolymerizable binder, (b) a pigment or a dyestuff, and (c) a photoinitiator of the formula

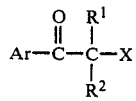

in which Ar denotes thioaryl or sulfinylaryl, and $R^1$ and $R^2$, in addition to a large number of other meanings, may also denote ($C_2$–$C_8$)-alkylene, while X is a (substituted) amino group. However, there is no mention of such cycloalkyl compounds in the text, and no experimental mention in the examples of the preparation of such compounds. No uses other than their suitability as photoinitiators are mentioned.

EP-A No. 164,246 discloses compounds of the formula

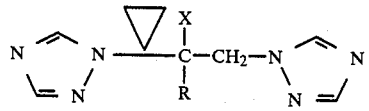

where X=OH (esterified or etherified), F, Cl or Br, and R=phenyl (unsubstituted or substituted) or 5-chloropyrid-2-yl, which have an antifungal action.

However, the action of these known compounds leaves something to be desired, particularly with respect to their antimycotic action.

The present invention was based on the object of preparing certain 1,1-disubstituted cyclopropane derivatives having a biologically important action, and also of developing simple processes for the preparation thereof. Surprisingly, the cyclopropane derivatives of the structure according to the invention have an antimycotic action or may be used as intermediates for the preparation of pharmaceutical preparations or stabilizers.

The invention is therefore directed at compounds of the formula (I)

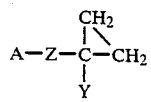

in which:

A denotes t-butyl, phenyl, biphenyl, phenoxyphenyl, benzyl-phenyl, benzyloxyphenyl, phenylthiophenyl, phenylsulfinyl-phenyl, phenylsulfonylphenyl, naphthyl, 1,2,3,4-tetra-hydronaphthyl, indanyl, fluorenyl, thienyl, furyl, pyridyl, isoxazolyl, pyrazolyl, benzofuryl or benzothienyl, where the ring systems mentioned may be unsubstituted or substituted by 1–3 substituents, which are identical or different and which are F, Cl, Br, I, ($C_1$–$C_8$)-alkyl, straight-chain or branched and unsubstituted or substituted by 1–9 F or Cl atoms, ($C_3$–$C_8$)-cycloalkyl, ($C_1$–$C_8$)-alkoxy, straight-chain or branched and unsubstituted or substituted by 1–9 F or Cl atoms, ($C_3$–$C_8$)-cycloalkyl-($C_1$–$C_4$)-alkyl, ($C_1$–$C_8$)-alkylthio, ($C_1$–$C_8$)-alkylsulfinyl, ($C_1$–$C_8$)-alkylsulfonyl, $NO_2$ or CN;

Z denotes

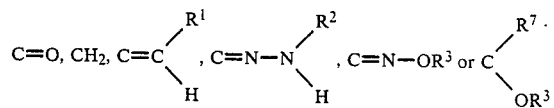

in which, in these Z groups, $R^1$ represents hydrogen, ($C_1$–$C_{12}$)-alkyl, cyano, ($C_1$–$C_{10}$)-alkoxycarbonyl, ($C_1$–$C_6$)-alkylcarbonyl, phenylcarbonyl or phenyl, in each case unsubstituted or mono- to trisubstituted by F, Cl or Br, the substituents being identical or different, $R^2$ represents hydrogen, ($C_1$–$C_4$)-alkyl, or phenyl which is unsubstituted or mono- to trisubstituted by F, Cl or Br, the substituents being identical or different, $R^3$ denotes hydrogen, ($C_1$–$C_6$)-alkyl, ($C_5$–$C_6$)-cycloalkyl, ($C_2$–$C_6$)-alkyl which is substituted by 1–3 chlorine or bromine atoms, ($C_2$–$C_6$)-alkenyl, unsubstituted, monosubstituted or disubstituted by chlorine or bromine, ($C_3$–$C_6$)-alkynyl, geranyl, farnesyl, ($C_1$–$C_4$)-alkoxycarbonyl-($C_1$–$C_3$)-alkyl, 1,2,4-triazolylmethyl, phenyl-($C_1$–$C_4$)-alkyl or phenoxy-($C_1$–$C_6$)-alkyl, phenyl or pyridyl, where the 4 lastmentioned groups are in each case unsubstituted or mono- to trisubstituted by F, Cl, Br, $CF_3$, ($C_1$–$C_4$)-alkyl, ($C_1$–$C_4$)-alkoxy, phenoxy, CN, $NO_2$, COOH or ($C_1$–$C_4$)-alkoxycarbonyl, the substituents being identical or different, $R^3$, however, alternatively represents the

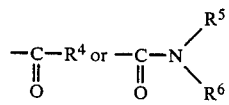

radicals, in which $R^4$ denotes ($C_1$–$C_6$)-alkyl, $C_5$- or $C_6$-cycloalkyl, ($C_2$–$C_6$)-alkenyl, phenyl, naphthyl, or phenyl-($C_1$–$C_4$)-alkyl, where the three lastmentioned radicals are unsubstituted or mono- to trisubstituted by F, Cl, Br, ($C_1$–$C_4$)-alkyl or ($C_1$–$C_4$)-alkoxy, the substituents being identical or different, or monosubstituted by a trifluoromethyl or trichloromethyl group, and $R^5$ and $R^6$ are identical or different and have the meanings of hydrogen, ($C_1$–$C_6$)-alkyl, or phenyl which is unsubstituted or mono- to trisubstituted by F, Cl or Br, but may not both simultaneously be H or phenyl, $R^7$ represents hydrogen, ($C_1$–$C_6$)-alkyl, ($C_2$–$C_3$)-alkynyl, phenylethynyl, benzyl or phenyl, where the phenyl radicals are in each case unsubstituted or substituted by 1 to 2 F, Cl or Br atoms or ($C_1$–$C_4$)-alkyl or ($C_1$–$C_4$)-alkoxy groups, the substituents being identical or different,

Y (a) denotes

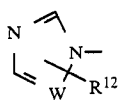

where
W=CH or N
and $R^{12}$ equals $(C_1-C_4)$-alkyl or $CF_3$,
(b) denotes $-X-R^8$
where
X= $-O-$, $-S-$, S=O or $SO_2$, and
$R^8=(C_1-C_{12})$-alkyl, straight-chain or branched $(C_3-C_8)$-cycloalkyl, $(C_3-C_8)$-cycloalkyl-$(C_1-C_4)$-alkyl, phenyl, biphenyl, phenoxy-phenyl, phenylthiophenyl, phenyl-$(C_1-C_4)$-alkyl, naphthyl, biphenyl-$(C_1-C_4)$-alkyl, phenylthiophenyl-$(C_1-C_4)$-alkyl, phenoxyphenyl-$(C_1-C_4)$-alkyl, naphthyl-$(C_1-C_4)$-alkyl, benzthiazol-2-yl, alkyl-benzimidazol-2-yl, N-$(C_1-C_4)$-alkylbenzimidazol-2-yl, pyridyl, pyrimidin-2-yl, furfuryl or thienyl-2-methyl, where the ring systems mentioned are unsubstituted or substituted by 1, 2 or 3 substituents, which are identical or different and in each case denote F, Cl, Br, I, $CF_3$, $(C_1-C_4)$-alkyl or $(C_1-C_4)$-alkoxy,
(c) denotes

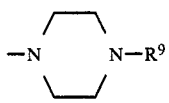

where $R^9=(C_1-C_8)$-alkyl, $(C_5-C_8)$-cycloalkyl, acetyl, phenyl or benzyl; where the phenyl nucleus is in each case unsubstituted or substituted by 1-3 F, Cl, Br or I atoms or $CF_3$, $(C_1-C_4)$-alkyl or $(C_1-C_4)$-alkoxy groups, which are identical or different,
(d) denotes

where $R^{10}$ and $R^{11}$ are identical or different and denote $(C_1-C_4)$-alkyl,
(e) denotes

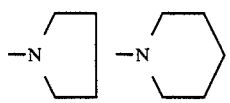

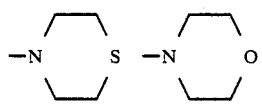

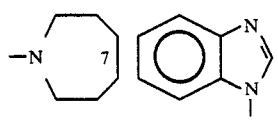

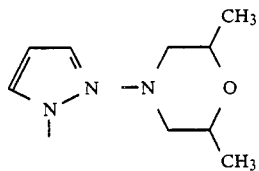

(f) denotes

$-OCR^{13}$, where $R^{13}$ equals $(C_1-C_8)$-alkyl, $(C_3-C_6)$-cycloalkyl, phenyl, benzyl or phenoxy-phenyl, where phenyl nuclei are in each case unsubstituted or substituted by 1-3 F, Cl, Br or I atoms or $CF_3$, $NO_2$, $(C_1-C_4)$-alkyl or $(C_1-C_4)$-alkoxy groups, which are identical or different,
and the salts thereof with physiologically acceptable acids, with the exception of the compounds in which
(a) simultaneously Z is C=O, A is phenyl and Y is $S-CH_3$ or S-phenyl; or
(b) simultaneously Z is C=O,
A is phenyl, optionally substituted by 1-3 substituents (which, independently of one another, are selected from F, Cl, Br, I, $CF_3$, $(C_1-C_4)$-alkyl and $(C_1-C_4)$-alkoxy) or 5-chloropyrid-2-yl and Y is 1,2,4-triazol-1-yl.

The invention also relates to salts or quaternization products of the compounds of the formula I which, through the presence of an N atom, are capable of forming such derivatives.

Preferred compounds of the formula I are those in which at least one of the substituents has the following meaning:
A: phenyl, biphenyl, 1,2,3,4-tetrahydronaphthyl, thienyl or indanyl, in each case unsubstituted or substituted in the aromatic ring by one or two substituents which are identical or different and in each case denote F, Cl, Br, $CF_3$, $(C_1-C_4)$-alkyl or $(C_1-C_4)$-alkoxy,
Y: (a)

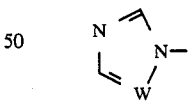

where W=CH or N
(b) $-X-R^8$ where
X=O or S, and
$R^8=(C_1-C_{12})$-alkyl, straight-chain or branched, phenyl, biphenyl, phenoxyphenyl, phenylthiophenyl, phenyl-$(C_1-C_2)$-alkyl, naphthyl, biphenyl-$(C_1-C_2)$-alkyl, naphthyl-$(C_1-C_2)$-alkyl, benzthiazol-2-yl, benzimidazol-2-yl, furfuryl or thienyl-2-methyl,
where the ring systems mentioned are unsubstituted or substituted by 1, 2 or 3 substituents which are identical or different and in each case denote F, Cl or Br atoms or $CF_3$, methyl or methoxy groups,
(c)

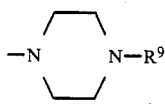

where $R^9$ = phenyl or benzyl, in each case unsubstituted or substituted by 1 or 2 F, Cl or Br atoms or $CF_3$, methyl or methoxy groups,

Z:

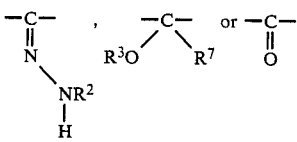

where $R^2$, $R^3$ and $R^7$ have the meanings mentioned.

Very particularly preferred compounds are those in which at least one of the substituents has the following meaning:

A: phenyl or thienyl, in each case unsubstituted or substituted by 1 or 2 F or Cl atoms or methyl or methoxy,

Y:

(a)

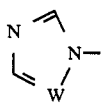

where W=CH or N (b) —X—$R^8$ where
  X=O or S, and
  $R^8$=($C_1$-$C_{12}$)-alkyl, straight-chain or branched, phenyl, benzyl, naphthyl or thienylmethyl, in each case unsubstituted or mono-or disubstituted by F, Cl, methyl or methoxy,

Z:

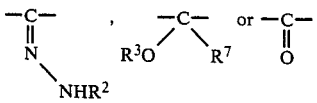

where $R^2$, $R^3$ and $R^7$ have the meanings mentioned, and the salts thereof with physiologically acceptable acids.

The cyclopropane derivatives of the formula I and the salts and quaternization products may, if certain substituents are chosen, have centers of chirality. The invention therefore covers mixtures of stereoisomers and also stereochemically unary compounds of the formula I.

The cyclopropane derivatives, according to the invention, of the formula I are capable, if they represent basic compounds, of forming salts or quaternization products. Salts of organic and inorganic acids, such as, for example, acetates, fumarates, oxalates, benzoates, phenolates, nitrates, bromides, chlorides, sulfates and sulfonates, and quaternization products with alkylacyl halides and optionally substituted phenylacyl halides may be mentioned.

The invention also relates to processes for the preparation of the compounds of the formula I, and also the salts and quaternization products thereof, wherein either (1) an ω-chlorohaloketone of the general formula II

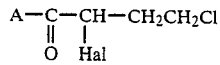

in which A has the meaning mentioned and Hal represents chlorine or, preferably, bromine, is reacted with a nucleophile of the formula III $$HY \qquad III$$

in which Y has the meanings mentioned, in the presence of an acid acceptor and, if appropriate, a diluent, or (2) in the case where Y is 1,2,4-triazol-1-yl or imidazol-1-yl, an azolyl ketone of the formula IV

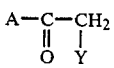

is reacted with 1,2-dibromoethane, if appropriate in the presence of a diluent and a phase-transfer catalyst, and the resultant compounds of the formula I, where Z equals C=O, if desired, are further converted by standard laboratory methods, and, if desired, are converted into their salts or quaternization products.

According to process 1, components (II) and (III) are expediently employed in approximately equimolar amounts. However, less than the equimolar amount of one or other component may also be used. The process is carried out at temperatures between 0° and 120° C., preferably at 20° to 90° C.

A procedure is followed here where either (a) a one-stage process in an aprotic dipolar solvent, preferably acetonitrile or dimethylformamide, in the presence of at least 2 moles of a base, preferably potassium carbonate, is used, or (b) a derivative of the formula V

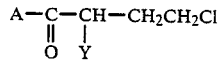

in which A and Y have the abovementioned meanings, is first prepared in acetone with at least 1 mole of base, preferably potassium carbonate, is, if appropriate, isolated and purified, and this is reacted in the presence of an aqueous solution of a strong, inorganic base, to which, if appropriate, an inert solvent, such as, for example, toluene, dichloromethane, xylene etc is added and which contains a phase-transfer catalyst. In this connection, a strong base is taken to mean preferably concentrated, aqueous sodium hydroxide solution or potassium hydroxide solution, preferably an at least 2 normal hydroxide solution.

Suitable phase-transfer catalysts are quaternary ammonium or phosphonium salts, crown ethers or polyethylene glycols. Such salts are known from the literature. Tetrabutylammonium bromide and benzyltriethylammonium chloride have proven particularly suitable for the present purposes.

According to process 2, the components IV and 1,2-dibromoethane are expediently employed in approximately equimolar amounts. However, less than the equimolar amount of one or other component may also be used. Temperatures between 30° 150° C., preferably 50° to 100° C., are used, in the presence of an acid acceptor in at least molar amount. The reaction is carried out here in the presence of an aqueous solution of a strong, inorganic base, to which, if appropriate, an inert solvent, such as, for example, toluene, 1,2-dichloroethane or xylene, is added, and which contains a phase-transfer catalyst. In this connection, a strong base is taken to mean preferably concentrated, aqueous sodium hydroxide solution or potassium hydroxide solution, preferably an at least 2 normal hydroxide solution. Suitable phase-transfer catalysts are those specified in the case of process 1b.

The ω-chlorohaloketones II serving as starting substances can be obtained by halogenation of corresponding ω-chloroketones. Examples which may be mentioned are: phenyl, 4-chlorophenyl, 4-phenylphenyl, 3-nitrophenyl, 1-naphthyl, 4-chloro-1-naphthyl, 1,2,3,4-tetrahydro-6-naphthyl, 2,5-dimethyl-3-methoxycarbonyl-4-furyl, 2-phenyl-5-furyl, 3-chlorothien-2-yl, 5-chlorothien-2-yl, 2,5-dimethylisoxazol-3-yl, 2-ethylbenzofuran-3-yl, 2-chlorobenzofuran-3-yl, benzothiophen-2-yl, benzothiophen-3-yl, 6-chloro-2-methoxycarbonylbenzothiophen-3-yl, 6-chloro-3-methylbenzothiophen-2-yl, isobenzofuran-1-yl, indolizin-1-yl and 1-methylindol-3-yl 1-bromo-3-chloropropyl ketone.

The nucleophiles of the formula III are generally known compounds of organic chemistry. Examples which may be mentioned are: 1,2,4-triazole, imidazole, pyrazole, benzimidazole, 4-chlorothiophenol, 3,4-dichlorophenol, benzoic acid, 5-(2-chloro-4-trifluoromethylphenoxy)-2-nitrobenzoic acid, piperidine, 1-phenylpiperazine and 2,6-dimethylmorpholine.

An example of the course of the reaction may be shown by the reaction of 1-bromo-3-chloropropyl 4-phenylphenyl ketone with 1,2,4-triazole:

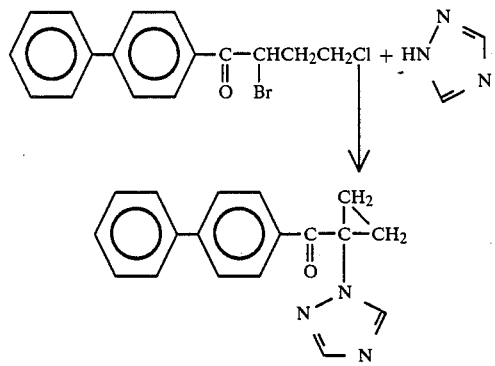

The smooth course of the reaction is surprising, since the formation of the monosubstitution products and the quaternization products must have been expected.

If desired, the ketones may be converted into further compounds according to the invention by standard laboratory methods, and these, if desired, are converted into salts or quaternization products by known methods.

The compounds of the formula I and their acid-addition salts are valuable medicaments or can be used as intermediates. In particular, they have an antimicrobial action and are suitable for the prevention and treatment of fungal infections in humans and in various species of mammal.

The new compounds have a very good action in vitro against dermatophytes, such as, for example, *Trichophyton mentagrophytes, Microsporum canis* and *Epidermophyton floccosum*; against mold fungi, such as, for example, *Aspergillus niger*, or against yeasts, such as, for example, *Candida albicans, C. tropicalis, Torulopsis glabratea* and *Trichosporon cutaneum*, or against protozoa, such as *Trichomonas vaginalis* or *T. fetus*, or against Gram-positive and Gram-negative bacteria.

After oral or parenteral administration, the compounds also have a very good systemic effect in vivo, for example in experimental kidney candidiasis of the mouse, for example against *Candida albicans*. There is likewise a very good effect against various pathogens of dermatomycosis (for example *Trichophyton mentagrophytes*) in guinea pigs after oral, parenteral or local administration.

The following may be mentioned as examples of areas of indication in human medicine:

Dermatomycoses and systemic mycoses caused by *Trichophyton mentagrophytes* and other Trichophyton species, Microsporon species, *Epidermophyton floccosum*, gemmiparous fungi, biphasic fungi and mold fungi.

The following may be mentioned as areas of indication in veterinary medicine:

All dermatomycoses and systemic mycoses, particularly those which are caused by the abovementioned pathogens.

The present invention includes pharmaceutical preparations which contain, besides nontoxic, inert pharmaceutically suitable excipients, one or more active compounds according to the invention or which comprise one or more active compounds according to the invention, and also processes for the preparation of these preparations.

Nontoxic, inert pharmaceutically suitable excipients are taken to mean solid, semisolid or liquid diluents, fillers and formulation auxiliaries of all types.

Suitable forms of administration are, for example, tablets, dragees, capsules, pills, aqueous solutions, suspensions and emulsions, optionally sterile injectable solutions, nonaqueous emulsions, suspensions and solutions, ointments, creams, pastes, lotions sprays etc.

The therapeutically active compounds should preferably be present in the abovementioned pharmaceutical preparations in a concentration from about 0.1 to 99.0, preferably from about 0.5 to 90% by weight of the total mixture.

In addition to the active compounds according to the invention, the abovementioned pharmaceutical preparations may also contain further pharmaceutical active compounds.

The abovementioned pharmaceutical preparations are prepared in a conventional fashion by known methods, for example by mixing the active compound or compounds with the excipient or excipients.

The present invention also includes the use of the active compounds according to the invention and of pharmaceutical preparations which contain one or more active compounds according to the invention in human and veterinary medicine for the prevention, improvement and/or curing of the above-mentioned disorders.

The active compounds or the pharmaceutical preparations may be administered locally, orally, parenterally, intraperitoneally and/or rectally.

In order to achieve the desired results, it has generally proven advantageous, both in human and in veterinary medicine, to administer the active compound or active compounds in total amounts of at least about 0.05, preferably 0.1, particularly 0.5, mg and at most 200, preferably 100, particularly 30, mg/kg of body weight per 24 hours, based on an adult weighing 75 kg, if appropriate in the form of several individual doses. The total amount is administered in 1 to 8, preferably in 1 to 3, individual doses.

However, it may be necessary to deviate from the dosages mentioned, and in particular to do so as a function of the type and body weight of the object to be treated, the nature and the severity of the disorder, the type of the preparation and administration of the medicament, and the period of time or interval within which the administration takes place. Thus, it may in some cases be sufficient to manage with less than the abovementioned amount of active compound, whereas in other cases the abovementioned amount of active compound, compound must be exceeded. The optimum dosage and type of administration of the active compounds required in each case can easily be determined by any expert on the basis of his expert knowledge.

EXAMPLE 1

Process version 1(a)

4-Phenylphenyl 1-(1,2,4-triazol-1-yl)-cyclopropyl ketone 44.7 g (0.648 mol) of 1,2,4-triazole and 89.5 g (0.648 mol) of anhydrous potassium carbonate were suspended in 525 ml of acetonitrile, and, under reflux, 202 g (0.6 mol) of of acetonitrile, and, under reflux, 202 g (0.6 mol) of 1-bromo-3-chloropropyl 4-phenylphenyl ketone were added in portions over 20 minutes. After a reaction time of 3 hours under reflux, the mixture was poured into ice water and the crystals obtained were filtered off under suction. 162.0 g (93% of theory) of colorless crystals of melting point 154°–5° C. were obtained.

EXAMPLE 2

Process version 1(b)

4-Chlorophenyl 1[4-(2-methoxyphenyl)-piperazinyl]cyclopropyl ketone 26.9 g (0.195 mol) of anhydrous potassium carbonate were suspended in 70 ml of acetone, 30 g (0.156 mol) of 1-(2-methoxyphenyl)-piperazine were added, and a solution of 38.5 g (0.13 mol) of 1-bromo-3-chloropropyl 4-chlorophenyl ketone dissolved in 50 ml of acetone was added dropwise at 0° C. with cooling. The mixture was allowed to stand overnight at room temperature, the salts were filtered off under suction, and the acetone was removed in vacuo. The residue was taken up in dichloromethane, washed by shaking with water and dried, and the solvent was removed. The oil remaining (52.9 g) was taken up in ethyl acetate, and the dihydrochloride was precipitated using hydrogen chloride.

38.5 g (62% of theory) of 3-chloro-1-[4-(2-methoxyphenyl-piperazinyl]-propyl 4-chlorophenyl ketone dihydrochloride of melting point 176° C. (ethanol) were obtained.

The salt thus obtained was suspended in 200 ml of dichloro-methane, 100 ml of 2 N sodium hydroxide solution were added, and the organic phase was separated off, treated with 29 ml of 50% strength sodium hydroxide solution and 2.2 g of benzyltriethylammonium chloride and stirred vigorously for 5 hours at 20° C. The mixture was diluted with water, the organic phase was separated off, washed with water and dried, and the solvent was removed in vacuo. The oil remaining crystallized with methanol.

Yield: 25.2 g (85% of theory) of the title compound of melting point 103°–104° C.

Preparation of the Starting Material
1-bromo-3-chloropropyl 4-phenylphenyl ketone 246 g (0.95 mol) of 3-chloropropyl 4-phenylphenyl ketone in 380 ml of glacial acetic acid were placed in a reaction flask and 152 g (0.95 mol) of bromine were added dropwise at 30° C., the reaction commencing with dissolution and decolorization. After 1 hour, a thick precipitate deposited. The mixture was stirred for a further 4 hours at room temperature in order to complete the reaction. The crystals produced were filtered off under suction, washed with water, dissolved in dichloromethane, washed by shaking with NaHCO$_3$ solution and water and dried, and 250 g (78% of theory) of the title substance were obtained as colorless crystals of melting point 85°–88° C.

EXAMPLE 3

Process version 2

1-Naphthyl 1-(1, 2, 4-triazol-1-yl)cyclopropyl ketone 20.7 g (0.1 mol) of (1, 2, 4-triazol-1-yl)-methyl 1-naphthyl ketone in 100 ml of dichloroethane, 0.3 g of benzyltriethyl-ammonium chloride and 27 ml of 50% strength sodium hydroxide solution were placed in a reaction flask and, under reflux, 20.7 g (0.11 mol) of 1, 2-dibromoethane were added dropwise over 15 minutes. The mixture was refluxed for a further 5 hours, cooled, diluted with water and extracted with dichloroethane. After drying and removing the solvent, 10.6 g (45% of theory) of the title compound were obtained as an oil.

EXAMPLE 4

4-Chlorophenyl-4-fluorophenyl-[1-(1, 2, 4-triazol-1-yl)-cyclo-propyl]-carbinol

4-Fluorophenylmagnesium bromide was prepared from 21.0 g (0.12 mol) of 4-fluorobromobenzene and 3.0 g (0.126 mol) of magnesium turnings in 60 ml of ether, and a solution of 15 g (0.06 mol) of 4-chlorophenyl 1-(1, 2, 4-triazol-1-yl)-cyclo-propyl ketone in 30 ml of tetrahydrofuran was added dropwise at room temperature. The mixture was refluxed for 2 hours, decomposed, with cooling, using saturated aqueous ammonium chloride solution, and extracted with dichloromethane. After removing the solvent by distillation in vacuo, 15.0 g (73% of theory) of the title compound remained as colorless crystals of melting point 183°–184° C. (from ethanol).

EXAMPLE 5

Ethyl 3-(4-phenylphenyl)-3-[1-(1, 2, 4-triazol-1-yl)-cyclo-propyl]-acrylate 17.4 g (0.06 mol) of the compound from Example 1 and 14.8 g (0.066 mol) of ethyl diethylphosphonylacetate in 66 ml of dimethylformamide were placed in a reaction flask and 1.98 g (0.066 mol) of 80% sodium hydride were added in portions. The reaction commenced with evolution of gas and warming and was terminated after stirring for 5 hours at 25° C. The mixture was poured into ice water, and 21.4 g (99%) of the title compound were obtained as brownish crystals of melting point 98°–100° C. by filtering off the resultant solids. Purification was effected by passing over a short silica gel column using $CH_2Cl_2$/ethanol=20:1 as eluant, melting point 140°–142° C.

EXAMPLE 6

4-Chlorophenyl 1-(1, 2, 4-triazol-1-yl)-cyclopropyl ketone hydrazone 37.1 g (0.15 mol) of 4-chlorophenyl 1-(1, 2, 4-triazol-1-yl)-cyclopropyl ketone were refluxed for 6 hours with 37.5 g (0.3 mol) of 80% strength hydrazine hydrate in 150 ml of ethanol. After removing the solvent by distillation in vacuo, 38.5 g (98%) of the title compound were obtained as a yellow oil.

EXAMPLE 7

1-(4-Chlorobenzyl)-1-(1, 2, 4-triazol-1-yl)-cyclopropane

A suspension of 24.8 g (0.1 mol) of 4-chlorophenyl 1-(1, 2, 4-triazol-1-yl)-cyclopropyl ketone with 19.8 g of 80% strength hydrazine hydrate in 40 ml of diethylene glycol was refluxed for 1 hour and cooled, and 14.3 g of powdered potassium hydroxide were added to the clear yellow solution. The mixture was refluxed, and the resultant water of reaction was then distilled off until the diethylene glycol again refluxed. After 1 hour, the mixture was poured into water and extracted with dichloromethane; after drying, the solvent was removed in vacuo and the residue remaining was distilled in a high vacuum. 13.5 g (57%) of the title compound were obtained as a yellowish oil, of boiling point 154°–156° C./0.05, which crystallized with melting point 67°–8° C.

EXAMPLE 8

4-Chlorophenyl 1-(1, 2, 4-triazol-1-yl)-cyclopropyl ketone oxime 24.8 g (0.1 mol) of 4-chlorophenyl 1-(1, 2, 4-triazol-1-yl)-cyclopropyl ketone were refluxed for 4 hours with 10.4 g of hydroxylamine hydrochloride, 10.6 g of sodium acetate in 200 ml of ethanol and 100 ml of water, the solvent was removed in vacuo, and the crystal slurry obtained was triturated with water. 21.7 g (83%) of the title compound were obtained as colorless crystals of melting point 186°–218° C.

EXAMPLE 9

4-Chlorophenyl 1-(1, 2, 4-triazol-1-yl)-cyclopropyl ketone oxime methylcarbamate 10 g (0.038 mol) of the compound obtained in Example 8 in 30 ml of acetone were placed in a reaction flask, and 2.9 g of methyl isocyanate and 2 drops of triethylamine were added. After refluxing for 3 hours, the suspended solid was filtered off under suction, and 2.9 g of starting material were isolated. 8.5 g (98%) of the title compound were isolated, as colorless crystals of melting point 116°–118° C., from the mother liquor by distilling off in vacuo.

EXAMPLE 10

4-Fluorophenyl 1-(1, 2, 4-triazol-1-yl)-cyclopropyl carbinol 1.2 g of sodium borohydride were added to a solution of 13.8 g (0.06 mol) of 4-fluorophenyl 1-(1, 2, 4-triazol-1-yl)-cyclopropyl ketone in 50 ml of methanol, the mixture was refluxed for 1 hour, and 12.4 g (89%) of the title compound, melting point 104°–106° C., were isolated by working up using dichloromethane/water.

EXAMPLE 11

4-Chlorophenyl-[1-(1, 2, 4-triazol-1-yl)-cyclopropyl]-methyl 4-trifluoromethylbenzyl ether 16.3 g (0.065 mol) of the compound obtained according to Example 61 were placed in 50 ml of dimethylformamide, 2.16 g of 80 percent sodium hydride were added, the mixture was stirred until the gas evolution was complete (about 1 hour), and 14.0 g of 4-trifluoromethylbenzyl chloride were added dropwise, the internal temperature increasing from 30° C. to 67° C. The mixture was heated at 80° C. for 4 hours and worked up using dichloromethane/water. Purification was effected by distillation; 23.1 g (87%) of the title compound were obtained as a yellowish oil of boiling point 195°–197° C./0.03.

The following compounds of the formula I were prepared according to Examples 1 to 11, but using appropriate compounds of the formulae II, III and I having Z=

$$\begin{array}{c} O \\ \| \\ -C- \end{array}.$$

| Example No. | A | Z | Y | b.p. (pressure) or m.p. (°C.) | Process version |
|---|---|---|---|---|---|
| 12 | 1-naphthyl | CO | $-N\begin{array}{c}N\\ \diagup \\ \diagdown \\ =N\end{array}$ .HNO$_3$ | 125 | 2 |
| 13 | 3,4-(CH$_2$)$_4$—C$_6$H$_{13}$ | " | " | 182–184 (0.04) | 1a |
| 14 | C$_6$H$_5$ | " | $-N\begin{array}{c}=N\\ \diagup \\ \diagdown \end{array}$ | 63–66 | 1b |

-continued

| Example No. | A | Z | Y | b.p. (pressure) or m.p. (°C.) | Process version |
|---|---|---|---|---|---|
| 15 | 4-CH$_3$O—C$_6$H$_4$ | " | " | oil | 1b |
| 16 | 4-F—C$_6$H$_4$ | " | " | 64–66 | 1b |
| 17 | 4-Cl—C$_6$H$_4$ | " | " | 69–70 | 1b |
| 18 | 2,4-Cl$_2$—C$_6$H$_3$— | " | ".HNO$_3$ | 158–60 | |
| 19 | 4-CH$_3$—C$_6$H$_4$ | " | " | 88–90 | 1b |
| 20 | 5-chloro-2-thienyl | " | 1,2,4-triazol-1-yl | 74–76 | 1a |
| 21 | 2,5-dimethyl-3-thienyl | " | " | 94–95 | 1a |
| 22 | " | " | imidazol-1-yl | 77–79 | 1a |
| 23 | 1,3-dimethyl-4-pyrazolyl | " | 1,2,4-triazol-1-yl | 152–4 / 0.06 | 1a |
| 24 | 4-Cl—C$_6$H$_4$ | " | S—C$_4$H$_9$ | 128 (0.1) | 1b |
| 25 | " | " | S—C$_8$H$_{17}$ | 170 (0.1) | 1b |
| 26 | " | " | SCH$_2$-(2-furyl) | 165–79 (0.1) | 1b |
| 27 | " | " | SCH$_2$C$_6$H$_3$—2,4-Cl$_2$ | 99–100 | 1b |
| 28 | " | " | SCH$_2$C$_6$H$_4$—4-Cl | 74–75 | 1b |
| 29 | " | " | S—C$_6$H$_4$—4-Cl | 104–105 | 1b |
| 30 | " | " | S—C$_6$H$_3$—3,4-Cl$_2$ | 65 | 1b |
| 31 | " | " | S—2-naphthyl | 82–84 | 1b |
| 32 | " | " | S-(2-pyridyl) | 103–104 | 1b |
| 33 | " | " | S-(2-pyrimidyl) | 110–111 | 1b |
| 34 | " | " | SO$_2$C$_6$H$_5$ | 101–102 | 1b |
| 35 | " | " | SO$_2$C$_6$H$_4$—Cl | oil | 1a |
| 36 | " | " | SO$_2$CH$_3$ | oil | 1a |
| 37 | " | " | 4-phenylpiperazin-1-yl | 132–133 | 1b |
| 38 | " | " | piperidin-1-yl | oil | 1b |

-continued

| Example No. | A | Z | Y | b.p. (pressure) or m.p. (°C.) | Process version |
|---|---|---|---|---|---|
| 39 | " | " | $OC_6H_4$—4-Cl | 69–71 | 1b |
| 40 | " | " | $OC_6H_3$—2,4-$Cl_2$ | oil | 1b |
| 41 | " | " | $OC_6H_3$—3,4-$Cl_2$ | oil | 1b |
| 42 | " | " | $OC_6H_4OC_6H_3$—2,4-$Cl_2$ | oil | 1b |
| 43 | 4-F—$C_6H_4$ | " | $SCH_2C_6H_4$—4-Cl | oil | 1b |
| 44 | 4-$CH_3$—$C_6H_4$ | " | " | oil | 1b |
| 45 | 4-$CH_3O$—$C_6H_4$ | " | " | oil | 1b |
| 46 | 4-$C_6H_5$—$C_6H_4$ | " | imidazolyl | 106–118 | 1a |
| 47 | 4-Cl—$C_6H_4$ | " | 2-methylimidazolyl | 171–176 (0.1) | 1a |
| 48 | 4-$C_6H_5$—$C_6H_4$ | " | pyrazolyl | 125–127 | 1a |
| 49 | 4-(4-F—$C_6H_4O$)$C_6H_4$ | | 1,2,4-triazolyl | 116–118 | 1a |
| 50 | 4-(4-Cl$C_6H_4O$)$C_6H_4$ | | " | 209–212 (0.04) | 1a |
| 51 | 4-$C_6H_5$—$C_6H_4$ | —C(=NNH$_2$)— | " | 160–161 | 6 |
| 52 | 5-Cl-2-thienyl | —C(=NNHC$_6H_5$)— | " | 91–93 | 6 |
| 53 | " | —C(=NOCH$_2$—$C_6H_4$—4Cl)— | " | oil | 8 |
| 54 | " | —C(=NOCH$_2$—$C_6H_4$—3-OC$_6H_5$)— | " | oil | 8 |
| 55 | " | —C(=NOCH$_2$—$C_6H_4$—4-$CF_3$)— | " | oil | 8 |
| 56 | 4-$C_6H_5$—$C_6H_4$ | —C(=NOH)— | " | 195–198 | 8 |
| 57 | 4-Cl—$C_6H_4$— | —CHOH— | 4-(2-methoxyphenyl)piperazin-1-yl | 79–81 | 10 |

-continued

| Example No. | A | Z | Y | b.p. (pressure) or m.p. (°C.) | Process version |
|---|---|---|---|---|---|
| 58 | " | " | ![piperazine-N-C6H5] N⟨piperazine⟩N—C$_6$H$_5$ | 114–116 | 10 |
| 59 | " | " | ⟨piperidine⟩·HCl | 231 | |
| 60 | C$_6$H$_5$— | —CH(OH)— | —N⟨1,2,4-triazol-1-yl⟩ | 111–112 | 10 |
| 61 | 4-Cl—C$_6$H$_4$— | " | " | 150–151 | 10 |
| 62 | " | —CH(O—CH$_2$—C$_6$H$_3$—2,4-Cl$_2$)— | " | oil | 11 |
| 63 | " | —C(CH$_3$)(OH)— | " | 153–5 | 4 |
| 64 | " | —C(C$_2$H$_5$)(OH)— | " | 143–145 | 4 |
| 65 | " | —C(C$_4$H$_9$)(OH)— | " | 157–159 | 4 |
| 66 | " | —C(4CH$_3$—C$_6$H$_4$)(OH)— | " | 192–193 | 4 |
| 67 | " | —C(C$_6$H$_5$—C≡C)(OH)— | " | 146–147 | 4 |
| 68 | 2,4-Cl$_2$—C$_6$H$_3$— | —CH(OH)— × HNO$_3$ | " | 144 (decomp.) | 10 |
| 69 | " | —C(4-F—C$_6$H$_4$)(OH)— | " | 204–207 | 4 |
| 70 | " | —C(C$_6$H$_5$C≡C)(OH)— | " | 153–155 | 4 |
| 71 | 4-C$_6$H$_5$—C$_6$H$_4$— | —CH(OH)— | " | 171–172 | 4 |
| 72 | 4-C$_6$H$_5$—C$_6$H$_4$— | —C(H)(O—OCH$_3$)— | —N⟨1,2,4-triazol-1-yl⟩ | 226/0.04 | 11 |
| 73 | " | —C(H)(O—CH$_2$C$_6$H$_4$—4-Cl)— | " | 266–70/0.2 | 11 |
| 74 | 4-(4-C$_6$H$_4$C)—C$_6$H$_4$— | —CH(OH)— | " | 138–141 | 10 |

-continued

| Example No. | A | Z | Y | b.p. (pressure) or m.p. (°C.) | Process version |
|---|---|---|---|---|---|
| 75 | " | —C(4-F—C₆H₄)(OH)— | " | 179–81 | 4 |
| 76 | Cl—[thiophene]—CH₃ (5-chloro-2-methylthiophene) | " | " | 195–197 | 4 |
| 77 | " | —C(4-Cl—C₆H₄)(OH)— | " | 160–163 | 4 |
| 78 | " | —CH(OH)— | " | 94–95 | 10 |
| 79 | H₃C—[thiophene(CH₃)]—  (2,5-dimethyl-3-methylthiophene) | —CH(OH)— | " | 92–94 | 10 |
| 80 | " | —C(C₆H₅C≡C)(OH)— | ".HNO₃ | 94 (Z) | 4 |
| 81 | 4-Cl—C₆H₄ | —CH(O—CH₂—C₆H₄—3-CF₃)— | " | 209–11/0.05 | 11 |
| 82 | " | —CH(O—CH₂—C₆H₃—2,6Cl₂)— | " | 225–8/0.05 | 11 |
| 83 | " | —CH(O—CH₂—C₆H₄—3-OC₆H₅)— | " | 241–5/0.02 | 11 |
| 84 | 2,4-(CH₂)₄—C₆H₃— | —CH(O—CH₂—C₆H₄—4-CF₃)— | " | 225–7/0.02 | 11 |
| 85 | " | —CH(O—CH₂—C₆H₄—3-CF₃)— | " | 221–4/0.05 | 11 |
| 86 | 4-Cl—C₆H₄— | —CH(O—CH₂—C₆H₄—2-CH₃)— | —N(N=CH—N=)— (1,2,4-triazol-1-yl) | 189–91/0.09 | 11 |
| 87 | 4-F—C₆H₄ | —CH(O—CH₂—C₆H₄—4-CF₃)— | " | 203–205/0.04 | 11 |
| 88 | 4-Cl—C₆H₄ | —CH(O—[2-pyridyl-5-CF₃])— | " | 94–96 | 11 |
| 89 | " | —CH(O—C₆H₄—4-CF₃)— | " | 213–7/0,05 | 11 |
| 90 | " | —CH(O—C₆H₃—2Cl—4-CF₃)— | " | 224–6/0.03 | 11 |

-continued

| Example No. | A | Z | Y | b.p. (pressure) or m.p. (°C.) | Process version |
|---|---|---|---|---|---|
| 91 | " | HO–C(C$_6$H$_4$–4-Cl)– | " | 174–6 | 4 |
| 92 | 2,4-F$_2$–C$_6$H$_3$– | HO–C(C$_6$H$_4$–4-F)– | " | 194–5 | 4 |
| 93 | 4-Cl–C$_6$H$_4$ | –CH(OCH$_2$–N(triazole))– | " | 111–2 | 11 |
| 94 | C$_6$H$_5$ | CO | –S–CH$_2$–C$_6$H$_4$–4-Cl | oil | 1b |
| 95 | 1-naphthyl | " | " | | " |
| 96 | 2-naphthyl | " | " | | " |
| 97 | 3,4-(CH$_2$)$_4$–C$_6$H$_3$ | " | " | | " |
| 98 | 3,4-(CH$_2$)$_3$–C$_6$H$_3$ | " | " | | " |
| 99 | 4-C$_6$H$_5$–C$_6$H$_4$– | " | " | | " |
| 100 | 4-(4-F–C$_6$H$_4$O)C$_6$H$_4$ | " | " | | " |
| 101 | 5-Cl-thiophen-2-yl | " | " | oil | " |
| 102 | " | " | –S–CH$_2$–C$_6$H$_5$ | | " |
| 103 | thiophen-2-yl | " | –N(1,2,4-triazol-1-yl) | oil | 1a |
| 104 | 3,4-(CH$_2$)$_3$–C$_6$H$_3$ | " | " | | " |
| 105 | 4-Cl–C$_6$H$_4$– | " | S–CH$_2$–C$_6$H$_5$ | oil | 1b |
| 106 | 4-Cl–C$_6$H$_4$ | " | –S–CH$_2$–C$_6$H$_4$–4-F | | " |
| 107 | " | " | –S–CH$_2$–C$_6$H$_4$–4-OCH$_3$ | | " |
| 108 | " | " | –S–(CH$_2$)$_2$–C$_6$H$_4$–4-Cl | | " |
| 109 | " | " | –S–CH$_2$–(2-naphthyl) | | " |
| 110 | " | " | –O–C$_6$H$_4$–C$_6$H$_5$ | 110–111 | " |
| 111 | 4-Cl–C$_6$H$_4$– | " | –O–CH$_2$–C$_6$H$_4$–4-Cl | | " |
| 112 | " | " | –O–CH$_2$–C$_6$H$_3$–2,4-Cl$_2$ | | " |
| 113 | " | " | –O–C$_6$H$_4$–4-CF$_3$ | | " |
| 114 | " | " | –N(piperazinyl-N'-C$_6$H$_4$–4-Cl) | | " |
| 115 | " | " | –S–CH$_2$–C$_6$H$_4$–3-Cl | | " |
| 116 | " | " | –S–CH$_2$–C$_6$H$_4$–2-Cl | | " |
| 117 | " | " | –S–CH$_2$–C$_6$H$_3$–2,6-Cl$_2$ | | " |
| 118 | 4-F–C$_6$H$_4$– | " | –S–CH$_2$–C$_6$H$_5$ | | " |
| 119 | " | " | –S–CH$_2$–C$_6$H$_4$–4-Cl | oil | " |
| 120 | " | " | –S–CH$_2$–C$_6$H$_3$–2,4-Cl$_2$ | | " |
| 121 | " | " | –S–CH–C$_6$H$_4$–3-Cl | | " |
| 122 | 4-F–C$_6$H$_4$– | " | –S–CH$_2$–C$_6$H$_4$–4-F | " | " |
| 123 | " | " | –S–CH$_2$–C$_6$H$_4$–4-OCH$_3$ | | " |

-continued

| Example No. | A | Z | Y | b.p. (pressure) or m.p. (°C.) | Process version |
|---|---|---|---|---|---|
| 124 | " | " | —S—CH₂—(naphthyl) | | " |
| 125 | " | " | —S—CH₂—C₆H₄—2-Cl | | " |
| 126 | " | " | —S—CH₂—C₆H₄—3-F | | " |
| 127 | " | " | —S—CH₂—C₆H₄—2-F | | " |
| 128 | " | " | —O—CH₂—C₆H₄—4-Cl | | " |
| 129 | " | " | —O—CH₂—C₆H₄—4-F | | " |
| 130 | 2,4-CH₂—C₆H₃— | " | —S—(CH₂)₃—CH₃ | 165–170 (0.1) | " |
| 131 | " | " | —S—CH₂—C₆H₄—4-Cl | | " |
| 132 | 2,4-F₂—C₆H₃— | " | —S—CH₂—C₆H₅ | | " |
| 133 | " | " | —S—CH₂—C₆H₄—4-Cl | oil | " |
| 134 | " | " | —N(imidazolyl) | | " |
| 135 | " | " | —S—CH₂—C₆H₄—4-F | oil | " |
| 136 | " | " | —O—CH₂—C₆H₄—4-F | | " |
| 137 | " | " | —S—CH₂—C₆H₃—2,4-Cl₂ | | " |
| 138 | 2,4-F,Cl—C₆H₃— | " | —S—CH₂—C₆H₄—4-Cl | 77–78 | " |
| 139 | 2,4-Cl,F—C₆H₃— | " | " | 62–63 | " |
| 140 | 3,5-Cl₂-thienyl | " | —S—CH₂—C₆H₄—4-Cl | | " |
| 141 | " | " | —N(imidazolyl) | | " |
| 142 | " | " | —N(1,2,4-triazolyl) | | 1a |
| 143 | 4-Cl—C₆H₄— | —CH—O—geranyl | —N(imidazolyl) | oil | 11 |
| 144 | " | —CH—O—CH₂—C₆H₄—4-Cl | " | " | 11 |
| 145 | 4-Cl—C₆H₄— | —CH—O—CH₂—C₆H₃—2,4-Cl₂ | " | 108 | " |
| 146 | " | —C(=CH₂)— | " | 94–95 | 5$^{(a)}$ |
| 147 | " | —C(=CH—C₆H₄—4-Cl)— | " | | " |
| 148 | " | —C(=CH—C₆H₃—2,4-Cl₂)— | " | 116–117 | " |

-continued

| Example No. | A | Z | Y | b.p. (pressure) or m.p. (°C.) | Process version |
|---|---|---|---|---|---|
| 149 | t-butyl | " | [1,2,4-triazol-1-yl: -N-N=N ring] | 114-115 | 2 |
| 150 | 4-Cl—C$_6$H$_4$ | " | —OC(=O)—CH$_3$ | 60-65 | 1b |
| 151 | 4-Cl—C$_6$H$_4$— | " | —O—C(=O)—C$_6$H$_4$-4-CH$_3$ | 113-13 | " |
| 152 | " | " | —O—C(=O)—C$_6$H$_4$-4-Cl | | " |
| 153 | " | " | —O—C(=O)—C$_6$H$_3$-2,4-Cl$_2$ | | " |
| 154 | " | " | —O—C(=O)—[2-nitro-4-(2-chloro-4-trifluoromethylphenoxy)phenyl] | | " |
| 155 | 2,4-F$_2$—C$_6$H$_3$ | " | [1,2,4-triazol-1-yl] | oil | 1a |
| 156 | " | —CHOH | " | 127-9 | 10 |
| 157 | " | —CH(OCH$_2$C$_6$H$_4$—4-CF$_3$)— | " | oil | 11 |
| 158 | 4-CH$_3$—C$_6$—H$_4$ | CO | " | 112-3 | 1a |
| 159 | 4-CH$_3$—O—C$_6$H$_4$ | " | " | 104-5 | " |
| 160 | 4-C$_6$H$_5$—C$_6$H$_4$ | CHOH | [imidazol-1-yl] | 190-1 | 10 |

[a] Prepared by reaction according to Example 5 of 1-(4-chlorobenzoyl)-1-(imidazol-1-yl)-cyclopropane with the appropriate triphenylphosphonium chlorides, using dimethyl sulfoxide as solvent.

Results of the treatment of laboratory animals infected experimentally with *Candida albicans* are given as an example of the high oral and parenteral in vivo action of the compounds according to the invention.

In order to determine the oral and parenteral action, groups each comprising 5 mice weighing 18–20 g (strain HOE: NMRKF; SPF 71) were infected with 2·10$^6$ germs/animal.

The animals were treated orally or subcutaneously in 8 identical individual doses each of 30 mg/kg or 10 mg/kg of body weight (−24/−18/−2h/+2/24/30/48/54h).

In addition to the group of 5 animals treated with the substances I according to the invention, a group likewise of 5 animals was treated for comparison with the reference substance ketoconazole. A control group of 10 animals was not treated after infection.

As can be seen from Table 2, the animals survived for up to twice as long after infection in the case of the compounds according to the invention, compared to the current standard preparation ketoconazole.

TABLE 2

| | | | | | | | | | |
|---|---|---|---|---|---|---|---|---|---|
| Dose | Example No. | Number of animals | Survival times days after infection | | | | Days x | Survival times in % (standard prep.: 100%) | |
| oral | 91 | 5 | 8 | 8 | 10 | 10 | 10 | 9.2 | 139.3 |
| 8 × 30 mg/kg | 4 | 5 | 9 | 10 | 10 | 10 | 10 | 9.8 | 148.4 |
| | ketoconazole | 5 | 6 | 6 | 7 | 7 | 7 | 6.6 | 100 |
| oral | 91 | 5 | 7 | 7 | 7 | 7 | 10 | 7.6 | 135.7 |
| 8 × 10 mg/kg | 4 | 5 | 8 | 10 | 10 | 10 | 10 | 9.6 | 171.4 |
| | ketoconazole | 5 | 5 | 5 | 5 | 6 | 7 | 5.6 | 100 |
| subcutaneous | 91 | 5 | 8 | 8 | 8 | 9 | 10 | 8.6 | 113.1 |
| 8 × 30 mg/kg | 4 | 5 | 10 | 10 | 11 | 11 | 12 | 10.8 | 142.1 |
| | ketoconazole | 5 | 7 | 7 | 7 | 8 | 9 | 7.6 | 100 |
| subcutaneous | 91 | 5 | 8 | 9 | 9 | 10 | 10 | 9.2 | 176.9 |
| 8 × 10 mg/kg | 4 | 5 | 8 | 11 | 12 | 13 | 14 | 11.6 | 223 |
| | ketoconazole | 5 | 5 | 5 | 5 | 5 | 6 | 5.2 | 100 |
| Controls, untreated infected animals | — | 10 | 1 2 | 1 2 | 1 2 | 1 2 | 2 3 | 1.7 | 27.2 |

We claim:

1. A compound of the formula I

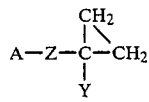

in which:

A is t-butyl, phenyl, biphenylyl, phenoxyphenyl, benzylphenyl, benzyloxyphenyl, phenylthiophenyl, phenylsulfinylphenyl, phenylsulfonylphenyl, naphthyl, 1, 2, 3, 4-tetrahydronaphthyl, indanyl, fluorenyl, thienyl, furyl, pyridyl, isoxazolyl, pyrazolyl, benzofuryl or benzothienyl, where the ring systems mentioned may be unsubstituted or substituted by 1–3 substituents, which are identical or different and which are F, Cl, Br, I, $(C_1-C_8)$-alkyl, straight-chain or branched and unsubstituted or substituted by 1–9 F or Cl atoms, $(C_3-C_8)$-cycloalkyl, $(C_1-C_8)$-alkoxy, straight-chain or branched and unsubstituted or substituted by 1–9 F or Cl atoms, $(C_3-C_8)$-cycloalkyl-$(C_1-C_4)$-alkyl, $(C_1-C_8)$-alkylthio, $(C_1-C_8)$-alkylsulfinyl, $(C_1-C_8)$-alkylsulfonyl, $NO_2$ or CN;

is

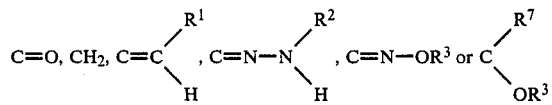

in which, in said Z groups, $R^1$ is hydrogen, $(C_1-C_{12})$-alkyl, cyano, $(C_1-C_{10})$-alkoxycarbonyl, $(C_1-C_6)$-alkylcarbonyl, phenylcarbonyl or phenyl, in each case unsubstituted or mono- to trisubstituted by F, Cl or Br, the substituents being identical or different, $R^2$ is hydrogen, $(C_1-C_4)$-alkyl, or phenyl which is unsubstituted or mono- to trisubstituted by F, Cl or Br, the substituents being identical or different, $R^3$ is hydrogen, $(C_1-C_6)$-alkyl, $(C_5-C_6)$-cycloalkyl, $(C_2-C_6)$-alkyl which is substituted by 1–3 chlorine or bromine atoms, $(C_2-C_6)$-alkenyl, unsubstituted, or monosubstituted or disubstituted by chlorine or bromine, $(C_3-C_6)$-alkynyl, geranyl, farnesyl, $(C_1-C_4)$-alkoxycarbonyl-$(C_1-C_3)$-alkyl, 1, 2, 4-triazolylmethyl, phenyl-$(C_1-C_4)$-alkyl or phenoxy-$(C_1-C_6)$-alkyl, phenyl or pyridyl, where the 4 last mentioned groups are in each case unsubstituted or mono- to trisubstituted by F, Cl, Br, $CF_3$, $(C_1-C_4)$-alkyl, $(C_1-C_4)$-alkoxy, phenoxy, CN, $NO_2$, COOH or $(C_1-C_4)$-alkoxycarbonyl, the substituents being identical or different, or $R^3$ is

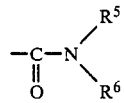

, in which $R^4$ is $(C_1-C_6)$-alkyl, $C_5$- or $C_6$-cycloalkyl, $(C_2-C_6)$-alkenyl, phenyl, naphthyl, or phenyl-$(C_1-C_4)$-alkyl, where the three last mentioned radicals are unsubstituted or mono- to trisubstituted by F, Cl, Br, $(C_1-C_4)$-alkyl or $(C_1-C_4)$-alkoxy, the substituents being identical or different, or monosubstituted by a trifluoromethyl or trichloromethyl group, and $R^5$ and $R^6$ are identical or different and are hydrogen, $(C_1-C_6)$-alkyl, or phenyl which is unsubstituted or mono- to trisubstituted by F, Cl or Br, but are not both simultaneously H or phenyl, $R^7$ is hydrogen, $(C_1-C_6)$-alkyl, $(C_2-C_3)$-alkynyl, phenylethynyl, benzyl or phenyl, where the phenyl radicals are in each case unsubstituted or substituted by 1 to 2 F, Cl or Br atoms or $(C_1-C_4)$-alkyl or $(C_1-C_4)$-alkoxy groups, the substituents being identical or different, Y denotes

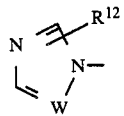

where

W is CH or N and $R^{12}$ is $(C_1-C_4)$-alkyl or $CF_3$ or H, or a salt thereof with a physiologically acceptable acid, with the exception of the compounds in which simultaneously Z is C=O, A is phenyl, unsubstituted or substituted by 1–3 substituents which, independently of one another, are selected from F, Cl, Br, I, $CF_3$, $(C_1-C_4)$-alkyl and $(C_1-C_4)$-alkoxy or is 5-chloropyrid-2-yl and Y is 1, 2, 4-triazol-1-yl.

2. A compound as claimed in claim 1, wherein at least one of the substituents has the following meaning:

A is phenyl, biphenylyl, 1, 2, 3, 4-tetrahydronaphthyl, thienyl or indanyl, in each case unsubstituted or substituted in the aromatic ring by one or two substituents which are identical or different and in each case are F, Cl, Br, $CF_3$, $(C_1-C_4)$-alkyl or $(C_1-C_4)$-alkoxy, Y is

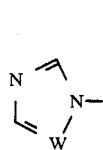

where W is CH or N

Z is

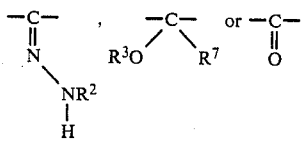

where $R^2$, $R^3$ and $R^7$ have the meanings recited in claim 1.

3. A compound as claimed in claim 1, wherein at least one of the substituents has the following meaning:

A is phenyl or thienyl, in each case unsubstituted or substituted by 1 or 2 F or Cl atoms or methyl or methoxy, Y is

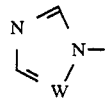

where W is CH or N

Z is

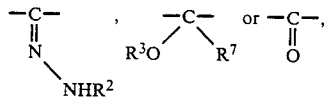

where $R^2$, $R^3$ and $R^7$ have the meanings recited in claim 1.

4. An antimicrobial composition comprising an effective antimicrobial amount of a compound of the formula I as claimed in claim 1 or a pharmaceutically acceptable salt thereof together with a pharmaceutically acceptable carrier.

5. A method for treating microbes in vitro which comprises administering thereto an effective antimicrobial amount of a compound of the formula I as claimed in claim 1 or a pharmaceutically acceptable salt thereof with or without a pharmaceutically acceptable carrier.

6. A method for treating a fungus in vitro or in vivo which comprises administering to the fungus or to a host in need of treatment an effective fungicidal amount of a compound of the formula I as claimed in claim 1 or a pharmaceutically acceptable salt thereof with or without a pharmaceutically acceptable carrier.

* * * * *